United States Patent [19]

Andersen

[11] Patent Number: 4,849,216

[45] Date of Patent: Jul. 18, 1989

[54] FLY ATTRACTANT

[75] Inventor: David A. Andersen, Long Beach, Calif.

[73] Assignee: Wescotek, Inc., Long Beach, Calif.

[21] Appl. No.: 946,370

[22] Filed: Dec. 24, 1986

[51] Int. Cl.$^4$ .................. A01N 25/00; A23L 00/00
[52] U.S. Cl. ........................................ 424/84; 426/1
[58] Field of Search ............... 424/84; 426/1; 435/42, 435/253, 254, 255, 942

[56]   References Cited

U.S. PATENT DOCUMENTS

| | | | |
|---|---|---|---|
| 3,846,557 | 11/1974 | Mulla et al. | 426/1 |
| 3,996,349 | 12/1976 | Mulla et al. | 424/84 |
| 4,369,176 | 1/1983 | Ott | 424/84 |
| 4,638,592 | 1/1987 | Schneidmiller | 426/1 |

FOREIGN PATENT DOCUMENTS 2928204  7/1978  Fed. Rep. of Germany ........ 424/84

OTHER PUBLICATIONS

Dethier, "Chemical Insect Attractants and Repellents", The Blakiston Company, Philadelphia, (1948), pp. 187–188.
Brown et al., "Chemical Attractants for the Adult House Fly", Jour. Econ. Ent., 54(4): 670–674, (1961).

Primary Examiner—Douglas W. Robinson
Assistant Examiner—Roger Gobrogge
Attorney, Agent, or Firm—Herb Boswell

[57]   ABSTRACT

A fly attractant composition includes a quantity of poultry protein wherein the poultry protein includes a quantity of at lesat one protein digestive microorganism capable of digesting the protein. This microorganism can either be native to the protein or it can be added as an inoculum. Further the composition contains a quantity of a carbohydrate which is capable of being fermented to yield carbon dioxide as a fermentation product. Additionally the composition contains a quantity of at least one carbohydrate fermentation microorganism which is capable of fermenting the carbohydrate to release carbon dioxide. When water is added to the fly attractant composition to form a fly lure, the carbon dioxide from the fermenting carbohydrate drives off odors from the ingredients which attracts flies to the lure.

19 Claims, No Drawings

FLY ATTRACTANT

BACKGROUND OF INVENTION

This invention is directed to an attractant for flies and similar insects for attracting these flies or similar insects to an appropriate bait or trap utilized to control these insects.

The house fly is a major nuisance to homeowners and in commercial areas such as food markets, food preparation areas, dairy barns and animal kennels. Throughout the years several methods have been utilized in an attempt to control the fly population in these areas.

One method used to attract flies involves hanging long strips of a sticky tape from a wall or ceiling. In their normal flying pattern, the flies land on the sticky tape and become permanently attached to it, thus reducing the population of the area. The tapes are rather unsightly which generally restricts their use to industrial or commercial applications.

Over the years several plastic or glass fly traps have been developed. These generally operate on the principle of a fly entering a trap through a funnel like opening and becoming entrapped within a glass or plastic container. The fly is unable to exit from the container because of the small hole at the narrow end of the funnel opening. An excellent plastic trap which utilizes this principle is described in U.S. Pat. No. 4,501,088.

In the traps of the type described in the previous paragraph which have been available to the consumer, the consumer has been instructed to bait the inside of the trap with a food component such as meat, fish or sugar water in order to attract the fly. This makes it somewhat inconvenient for the user of the trap because of the need to maintain quantities of such ingredients on hand. Further, odors emitted by the putrefaction of these components can frequently be very obnoxious thus reducing the number of locations where the traps can be used.

There are many species of flies. The common house fly is scientifically known as Musca Domestica. Other common flies are the Little House Fly, the Blow Fly and the various bottle flies. Collectively these are known as domestic or filth flies. They are generally associated with man and his environment. They live and breed in waste and garbage. Aside from being annoying and repulsive, flies are suspected of transmitting many diseases.

The domestic or filth fly lay their eggs in any warm moist material where their larvae can grow. Such material might be animal waste, garbage, lawn clippings, rotting fruit and vegetables, rotting grains, manures, carcasses of dead animals or any meat product. Breeding and egg laying is started whenever the temperatures are sufficiently warm and breeding material is available. The eggs can hatch within a day and the larvae can pupate after a week or less. The pupal stage can last from 4 to 6 days at which time the adult fly emerges. This adult fly can lay upwards of 600 eggs and is capable of traveling over a geographical area of many square miles. As evident from the above, the complete life cycle under optimum conditions, can be completed in approximately 8 days making the fly a very prolific pest.

Within the last few years certain insects sex hormones generically referred to as pheromones have been developed for use in attracting various insects. Each insect has its own unique pheromones. For many agricultural type insects for which pheromones have been developed, the use of these pheromones have been very successful in controlling the insects. The pheromones are useful because they disrupt the mating cycle of the insects by confusing the male insect with respect to the location of the female insects.

With flies the current state of the art of pheromones is not as developed as for other insects. One such fly pheromone is described in U.S. Pat. No. 4,122,165 and is sold under the commercial name Muscamone TM. The main difficulty with pheromones for fly lures is the fact that they are only strong enough to attract flies from a very short distance from a trap. In many cases the fly must land almost right on or in close proximity to the fly pheromone before it becomes attracted to it.

BRIEF DESCRIPTION OF THE INVENTION

This invention provides an insect attractant especially a fly attractant. This attractant can be utilized in the vicinity of poisonous bait or can be located within an insect trap to attract the insects to the trap. The fly attractant of the invention is composed of all natural ingredients which are nontoxic. The attractant is easily prepared and is suitable for long term storage while at the same time providing for an effective, easily used and economically available product.

This can advantageously be achieved in a fly attractant composition which comprises a quantity of a poultry protein, the poultry protein including a quantity of at least one residual microorganism capable of digesting the protein, a quantity of a carbohydrate of a type capable of being fermented to yield carbon dioxide as a fermentation product and a quantity of at least one carbohydrate fermentation microorganism wherein the microorganism is capable of fermenting the carbohydrate to release carbon dioxide.

Useful as the poultry protein will be poultry body parts as for instance chicken or turkey parts including poultry livers, dehydrated whole ground chicken and dehydrated whole ground turkey, dehydrated chicken broth, dehydrated turkey broth, dehydrated chicken giblets, dehydrated turkey giblets, dehydrated chicken viscera and dehydrated turkey viscera. Particularly advantageous protein soruces are dehydrated and freeze dried chicken livers.

The poultry protein would include a quantity of naturally occuring microorganisms and/or enzymes capable of digesting the poultry protein or if the protein is sterile, a quantity of such organisms is added to the poultry protein for digesting the poultry protein. The protein source can be digested for a period of time and then dried and packaged with the remaining ingredients or a sterile protein source can be inoculated with suitable digestion microorganisms and packaged with the remainder of the ingredients.

The carbohydrate source will be chosen to be one of a variety of carbohydrates which is capable of being fermented to release carbon dioxide. This would include natural sugars and starches including spray-dried or drum-dried honey or other powdered honey, sugars involving surcrose, fructose, glucose, dehydrated corn syrup solids, lactose, maltose or dehydrated molasses. It can also include dehydrated fruit powders having high levels of natural sugars as for instance, raisin solids, dehydrated date juice, banana powder or apple powder. A particularly advantageous carbohydrate source is dehydrated honey.

The carbohydrate fermentation microorganism is chosen from those organisms capable of fermenting the above carbohydrate sources or other carbohydrate sources to release carbon dioxide as a fermentation byproduct. Such organisms include yeast and bacteria. As for instance, suggested as suitable species of yeast are *Saccharomyces Cerevisiae* and *Saccharomyces Carlsbergenis* and suggested as suitable bacterium are Eschericha, Clostridium, Lactobacillus, Aerobacter, Bacillus and Leuconostoc. Particularly advantageous are the above referred to yeasts, most particularly *Saccharomyces Cerevisiae*.

An advantageous fly lure comprises a quantity of a carbohydrate which is capable of being fermented to yield carbon dioxide as a fermentation byproduct; a quantity of at least one carbohydrate fermentation microorganism wherein the microorganism is capable of fermenting the carbohydrate material; a quantity of a poultry protein including the poultry protein containing a quantity of at least one digestion microorganism capable of digesting and/or degrading the poultry protein; and a quantity of water. These ingredients are placed in a container. The container would serve as a reservoir for the carbohydrate material, the protein and its digestion organisms, the carbohydrate fermentation microorganisms and the water and would further contain an opening for releasing odors from the container to the atmosphere.

The invention described in this specification utilizes certain principles and/or concepts as are set forth in the claims appended to this specification. Those skilled in the insect attractant arts will realize that these principles and/or concepts are capable of being utilized in a variety of embodiments which may differ from the exact embodiments utilized for illustrative purposes in this specification. For this reason this invention is not to be construed as being limited solely to the illustrated embodiments but should only be construed in view of the claims.

DETAILED DESCRIPTION OF THE INVENTION

One way of attempting to deal with the problem of insect pests such as flies is to eliminate anything which might attract them. This can be done by being very judicious about keeping lids on garbage cans, keeping doors or windows closed or screens on these doors or windows or other expedients. While this may be practical in certain settings such as a household residence, in other situations such as restaurants and the like where there is a lot of traffic and doors are continually being opened and closed or in open situations such as in animal storage pens, barns and the like, this is simply not possible.

In attempting to control flying insects such as flies, sprays are not as effective as they are in controlling crawling insects simply because of the mobility and the range of the insects. Further, many people are adverse to the use of toxic insecticides. Additionally insecticide sprays generally have obnoxious residual smells.

In order to attract flies and other similar insects to mechanical traps or to concentrated poisonous bait it is necessary to provide an attractant or lure which will lead the flies to the trap or to the bait. Fresh scraps or garbage tend to dry out and become ineffective in a very short period of time or they decompose emitting very obnoxious odors which are very objectionable. Because of this traps or poison bait which utilize such scraps or garbage as lures or attractants must continually have the lure or attachment replenished at a fairly regular basis in order to be effective. Further because of their odors, generally they are not useful in areas where food is consumed.

I have found that a very effective fly attractant composition and a lure which utilizes this composition is achieved by using a carbohydrate material in conjunction with a microorganism capable of fermenting this carbohydrate material to release carbon dioxide gas further in conjunction with a poultry protein source which either has natural microorganisms inherent in this source for the digestion of this source and/or an addition of these microorganisms to a sterilized poultry protein source. These ingredients can be blended as a dry powder for storage and upon the addition of water to this powder activation of the fly lure is achieved. Because of this the fly attractant is capable of being stored for long periods of time as for instance for manufacturing and distributing and/or consumer storage without any loss of its functionality. This makes it possible to supply an attractant or lure package with the sale of a commercial fly trap and further to utilize the fly attractant in time release membrane packages for sustained but effective release of the attractant over long periods of time.

An additional advantage of the fly attractant and lure of this invention is the manner in which it can be very sanitarily packaged for distribution and use by the consumer in a variety of situations such as in the home or in food establishments.

The fly attractant is capable of being stored for very long periods of time upwards of several years without loss of its functionality and is further capable of attracting or luring insects to its proximity for a prolonged period of time as for instances weeks. Further, as opposed to the use of decomposing scraps or garbage as an attractant, both during storage and use the attractant of the invention has an agreeable odor.

The fly attractant and lure of the invention are capable of being packaged in packages, including time release packages, which are conveniently used in various plastic or glass fly traps or for attracting high concentrations of flies to chemically baited material which will kill flies or maggots when they eat the chemically baited material. The attractant is capable of being manufactured and stored in bulk or divided into individual packets for use with appropriate fly traps as for instance, the fly trap described in U.S. Pat. No. 4,501,088 mentioned above.

The operation of the attractant or lure is as follows. A poultry protein source having a natural inoculum of digestion microorganisms or an artificial inoculum of these organisms is mixed with a carbohydrate and a microorganism capable of fermenting the carbohydrate to release carbon dioxide. Depending upon the carbohydrate source it might have a natural odor as for instance the nectar type odor from honey. This natural odor will further serves as an attractant for the flies. The microorganism for fermenting the carbohydrate source also might have volatile odors which are known to attract flies as for instance the volatile odors of yeast.

Irrespective of whether or not the carbohydrate source and/or the fermentation organism for the carbohydrate source have such attractant odors, when the ingredients are mixed with water the fermentation organism for the carbohydrate will ferment the carbohydrate producing carbon dioxide and the digestive organisms in the poultry protein will modify the protein. The carbon dioxide produced from the material of the fly attractant composition volatilizes the odors of the fermenting/digesting mixture producing a positive pressure within this mixture to positively release the odors of the mixture to the atmosphere for attracting flies to the odor.

While I do not wish to be bound by theory it is my belief that the fermentation/digestion of the above referred to blend of the poultry protein, the carbohydrate and the carbohydrate fermentation microorganism appears to release volatile aldehydes, ketones, mercaptans and amines which are detected by the flies and which serve as strong attractants for the flies.

In use the fly attractant composition as a dry powder is mixed with a small amount of water to initiate fermentation/digestion. Within a very short period of time of from about 2 to 3 hours the material gives off an agreeable odor and begins to attract flies. The product will function as long as its takes for evaporation of all the water which can be anywhere from several days to several weeks depending upon temperature, relative humidity and other environmental factors. Additionally, the lure will be effective longer if the attractant is utilized in conjunction with time release membranes.

I have found that poultry protein as for instance protein from chickens or turkeys to be vastly superior to other proteins as the protein source for the invention. The poultry protein can be derived utilizing dehydrated whole ground chicken or turkeys, dehydrated chicken or turkey broth, dehydrated chicken or turkey giblets, dehydrated chicken or turkey viscera or preferably dehydrated chicken or turkey livers, especially chicken livers, more particularly chicken livers from fryers. These products have been found to be vastly superior to either fish base or beef base products. I presently prefer to use the livers from chicken fryers. Only slightly less effective than livers from chicken fryers are the livers from stewing chickens and from turkeys. For the purposes of this specification, whole ground poultry is considered to be cleaned poultry carcasses. Further giblets are normally the edible internal organs and viscera the remainder of the internal organs.

After harvesting of the protein source from the poultry the protein source is either allowed to naturally digest and/or ferment for a period of time or if it had been treated in a manner to sterilize this natural protein source, an inoculum of an appropriate microbiological broth containing bacteria and/or enzymes is added to the poultry protein for digestion and/or degradation of the poultry protein during the use of the fly attractant composition and/or lure.

There are several alternative methods for preparation of the protein faction of the fly attractant. A first of these would include emulsifying the poultry body part and allowing it to digest for a time period in order to achieve a high bacterial profile within this material. The semi-spoiled material is then freeze-dried for use as the poultry protein portion of the fly attractant. The freeze dying does not destroy the native microorganism (bacteria/enzymes) in the poultry protein and these organisms are activated again once water is added back to this freeze-dried protein.

A further method of preparing the poultry protein is by spray-drying or otherwise drying the emulsified poultry product. A small inoculum of freeze-dried fermented chicken liver as a digestion microorganism source is added to this relatively sterile dried material.

It is also possible to totally sterilize liquefied, emulsified poultry protein tissue followed by cooling to a proper fermentation temperature and inoculation with a bacterial culture which has been initially isolated from a poultry base. In any event there will be a quantity of a poultry protein present and a quantity of at least one microorganism either natural to the poultry protein or added to it which is capable of digesting and/or degrading this poultry protein.

The fly attractant composition of the invention therefore contains a poultry protein component with a residual amount of bacteria normally present in the poultry flesh which is either maintained in the poultry protein itself or is added as an inoculum to that poultry protein. For understanding of this specification and the claims attached hereto in order to characterize the microbiological process on the poultry protein from those on the carbohydrate (discussed below), the terminology "digestion" and variants thereof will be utilized to describe the process by which the bacteria and/or enzymes breakdown, degrade, digest and/or ferment the poultry protein while the terminology "fermentation" and variant thereof will be utilize in connection with the carbohydrate.

A particularly useful poultry protein consists of chicken livers which are emulsified and then allowed to naturally digest at a temperature between 50° to 75° F. for 2 to 5 days. During this time period bacteria naturally present in the chicken livers such as pseudomonads and various micrococci such as streptococci, pediococci and microbacteria will reproduce. After the digestion period the product has a cheesy type of fermentation odor. It is then frozen and freeze-dried or lyophilized into a semi-solid sheet which is ground to a powder prior to mixing with the other ingredients of the invention. During this process all of the natural enzymes, bacteria and odors existing in the digested chicken liver remain relatively intact and functional.

Typically the poultry protein component of the composition (including its digestion microorganisms) will be utilized in an amount from about 25 to about 80% by weight for the total dry weight of the fly attachment composition. The lower limit of the poultry protein fraction is based upon the amount of protein necessary to be present in order for the base to be effective over a reasonable time period. The upper limit is based upon allowing for a sufficient quantity of the carbohydrate and microorganisms for fermenting that carbohydrate to produce sufficient carbon dioxide for dispersion of the odors emanating from the fly lure of the invention.

The carbohydrate present in the fly attractant composition can be any one of a number of carbohydrates available from various sources which are capable of being fermented to release carbon dioxide as a fermentation product. Additionally the carbohydrate can be selected as a carbohydrate having a naturally occurring odor which tends to attract flies. Preferably the carbohydrate would be utilized in powder form for convenience of manufacturing, packaging and storing of the fly attractant of the invention.

Suitable for the carbohydrate source is dehydrated honey which may be either spray dried or drum dried or as available in commercial powdered form on a carrier such as a starch or low dextrose corn syrup solid. Additional carbohydrate sources include sucrose, fructose, glucose, dehydrated corn syrup solids, lactose, maltose, dehydrated molasses and dehydrated fruit powders containing high levels of natural sugars such as raisin solids, dehydrated date juice, banana powder and apple powder. Of these presently preferred for use is honey, fructose or dehydrated molasses. Honey is especially useful because of its natural fly attracting odor.

The carbohydrate source will be used in an amount of from about 5% to about 40% by weight per the total dry weight of the the solid components of the fly attractant composition. A preferred range would be from about 15% to about 30%. Below about 5% there is insufficient carbohydrate material for the production of sufficient amounts of carbon dioxide for effective dispersal of the odors of the digesting poultry protein. Above about 40%, once water is added to the dry products of the fly attractant composition, the osmotic pressure of the system is sufficiently high to limit the growth of the organism utilized for fermentation of the carbohydrate fraction. In the range of from about 15 to about 30% there is ample carbohydrate present for excellent production of carbon dioxide but not such an excessive amount that the osmotic pressure starts to inhibit the carbohydrate fermentation microorganism growth.

Suitable for the fermentation microorganism for the carbohydrate is any microorganism capable of fermenting the carbohydrate source and yielding carbon dioxide as a fermentation byproduct. Generally such microorganisms would include yeasts and bacteria. The particular microorganism or a mixture of microorganisms chosen would take into account the carbohydrate source so as to optimize the release of carbon dioxide from this carbohydrate source. Suitable as microorganisms for the fermentation of the carbohydrate source are Saccharomyces Cerevisiae and Saccharomyces Carlsbergenis which are both yeasts and Eschericha, Clostridium, Lactobacillus, Aerobacter, Bacillus and Leuconostoc which are bacteria.

It is preferred however to use a yeast as the carbohydrate fermentation microorganism in so far as during fermentation of the carbohydrate source certain natural fermentation odors are emitted from the yeast which serve as additional attractants for flies. Thus with yeast as the fermenting species for the carbohydrate component not only is carbon dioxide produced but its natural fly attracting fermentation odors are also produced. It is recognized that in addition to the two yeast species noted above that other yeast species could be utilized for the fermentation of the carbohydrate component.

As used, the microorganism for fermenting the carbohydrate component would be present from about 1% to about 40% by weight per the dry weight of the fly attractant composition. It is recognized that if the fly lure is utilized at a temperature which is optimum for the growth of this microorganism a smaller amount of the microorganism can be used and if used in environments which are not conducive to rapid growth of the microorganism, greater amounts are suggested. While amounts greater than 40% noted above could be utilized, by utilizing the additional amounts of this microorganism component it would require use of lesser amounts of the carbohydrate and protein fractions. This would detract from the properties those components contribute to the fly lure of the invention. At a range of from about 10% to about 30% by weight of the microorganism per dry weight of the fly attractant composition, a sufficient amount is present for fermentation of the carbohydrate component under a variety of environmental conditions for the production of suitable amounts of carbon dioxide for volatilization of the odors of the ingredients of the fly lure.

For both the microorganism necessary for fermentation of the carbohydrate component and the microorganisms necessary for digestion/degradation of the poultry protein component, as is recognized in the microbiological arts, a different exact weight amount of either of these components can have different microorganism cell counts per amount of component. The above referred to amounts of both the carbohydrate fermentation microorganism and the poultry protein having its digestion fauna present therein take into account the variability of the cell count per gram of these ingredients.

I have found that acceptable lures are produced which are capable of catching a large number of flies which have protein digestion bacteria cell counts as low as one half million bacterium per gram and as high as several billion per gram. Further utilizing yeast as the carbohydrate fermentation microorganism, successful lures have been produced which have yeast cell counts in a range as low as 5 million cells per gram to as high as 150 million yeast cells per gram.

Insofar as an end byproduct of the biochemical reactions on the fly attractant composition of the invention are odors emitted from the fly lure of the invention, contrary to edible consumer product such as bread or the like, there is a degree of variability in the exact amounts of these components which necessarily have to be present. In any event what is necessary is a sufficient amount of the carbohydrate fermentation microorganism being present to ferment the carbohydrate material to produce carbon dioxide and further for the poultry protein fraction to contain a sufficient amount of microorganisms therein for digestion of this component but the amounts of these two components must not be so excessive so as to dilute the other components of the fly attractant down below levels where they detract from the efficiency of the fly lure.

The activate the fly attractant composition of the invention for use in a fly lure of the invention, the dry ingredients of the composition are wet with water. With the addition of water, the above discussed microbiological fermentation and digestion process of the carbohydrate and poultry protein, respectively, are started. Upon initiation of these microbiological processes odors are emitted from the lure which attract flies.

The dry ingredients comprising the fly attractant composition, i.e. the carbohydrate, the carbohydrate fermentation microorganism and the poultry protein having it digestive microorganisms located therein, are utilized with amounts of water such that they will be present in amounts from about 10% solids in the water to about 50% solids in the water. In amounts greater than about 50% solids in the water, the above discussed increases in osmotic pressure of the carbohydrate component tend to inhibit the action of its fermentation microorganism and below about 10% solids in the water, the amount of water is such that fermentation of the carbohydrate is slow which reduces the amount of vapors emitted by the lure.

The following are given as representative examples of fly lures:

EXAMPLE 1

Five pounds of poultry fryer chicken livers were emulsified into a paste utilizing a Hobort vertical blade emulsifier. BHT at a level of 0.01% was added to the emulsified chicken liver as an antioxidant to prevent oxidation of fat in the emulsified chicken liver during long term storage. The emulsified mass was allowed to naturally digest at a refrigerated temperature of 50° F for five days. After digestion the material was frozen and freeze dried. The freeze dried solid was ground to a powder. To 50 grams of the powdered freeze dried digested chicken livers was added 20 grams of dehydrated honey powder and 30 grams of food grade yeast (*Saccharomyces Cerevisiae*). These dried ingredients were blended together and packaged into packets containing about 12 grams of the dried ingredients per packet. The freeze dried poultry liver powder had a bacteria count of about 45 million per gram.

For use an above packet having about 12 grams of dried ingredients was dissolved into 2 to 3 ounces of water and set aside to initiate fermentation and further digestion. Within approximately 2 to 3 hours the material gave off an odor and began attracting flies.

The above wetted powder was placed in a fly trap of the type described in U.S. Pat. No. 4,501,088 in the patio area of a residential home for a period of 5 days. At the completion of this test period the trap contained 513 flies.

EXAMPLE 2

Spray-dried chicken liver was produced by emulsifying fresh fryer chicken liver and liquefying the material with 1% papain at a temperature of 135° F. for 1 hour. The liquefied liver was then spray-dried in a commercial spray-dryer resulting in a dehydrated chicken liver powder. 49 grams of this dehydrated chicken liver powder was mixed with one gram of the digested freeze dried fermented chicken liver as per Example 1 above. To this was added 30 grams of food yeast and 20 grams of dehydrated honey powder. The blended product had a bacterial cell count of 800,000 per gram.

12 grams of the above powder was mixed with 30 grams of water and was loaded into the trap as identified in Example 1 and used in the same area as in Example 1. After a seven day period there were 474 flies caught in the trap.

EXAMPLE 3

Emulsified chicken livers were directly freeze dried without digesting as noted in Example 1. The freeze dried product was ground to a fine powder. 45 grams of this freeze dried fresh chicken liver powder was admixed with 5 grams of digested dried fermented chicken liver as per Example 1. To this was added 30 grams of food yeast and 20 grams of dehydrated honey powder.

The final powder had a bacterial cell count of 3.4 million organisms per gram. The above material was tested in the same trap and location as in Example 1. After a period of 7 days 1,416 flies were caught in the trap.

EXAMPLE 4

20 grams of non-fat dry milk powder, 1 gram of yeast extract and 79 grams of water were sterilized at 250° F. for 15 minutes. The culture was cooled to 100° F. and inoculated with a composite of 5 unidentified microorganisms, indigenous to chicken liver, which had been originally isolated using standard microbiological techniques from fresh chicken liver. The culture was incubated for 24 hours at which time it had a bacterial cell count of 4.3 billion organisms per gram. The resulting culture was freeze-dried to a powder. The powder contained 1.4 billion bacteria cells per gram. 5 grams of this powder was added to 45 grams of spray-dried chicken liver as per Example 2 above. To this was added 30 grams of food yeast and 20 grams of dehydrated honey powder.

12 grams of the above powder was mixed with 30 grams of water and utilized in the same trap and at the same location as per Example 1. After a period of 7 days 976 flies were caught in the trap.

As is evident from the above examples the fly attractant composition can be successfully used in a method of attracting flies by choosing a poultry protein and including a quantity of protein digestive microorganism within the protein. This can of course be either natural to the protein or can be added as an inoculum. This is augmented by choosing a carbohydrate and at least one microorganism for fermentation of the carbohydrate to produce carbon dioxide as a byproduct and mixing these with the protein and its digestion microorganism. At this point the mixture of ingredients is stable for long term storage. It is activated by wetting it with water and exposing the wetted mixture to the atmosphere for venting fermentation and digestion vapors from the mixture to the atmosphere for attracting the flies.

The above method is particularly useful as an attractant for mechanical fly traps.

I claim:

1. A fly attractant composition consisting of:
   an attractive effective amount of poultry liver for generating an attractive odor, said poultry liver including a digestive quantity of at least one poultry protein digestive microorganism capable of digesting said liver;
   a carbon dioxide producing effective amount of a carbohydrate selected from the group consisting of dehydrated honey, fructose and dehydrated molasses for generating a positive pressure upon fermentation, said carbohydrate capable of being fermented to yield carbon dioxide as a fermentation product;
   a fermentative quantity of at least one carbohydrate fermentation microorganism, said microorganism capable of fermenting said carbohydrate to release carbon dioxide.

2. A fly attractant composition of claim 1 wherein:
   said protein digestive microorganism comprises a native microorganism which is residual in said poultry liver.

3. A fly attractant composition of claim 1 wherein:
   said protein digestive microorganism comprises an inoculum of a liver digestive microorganism added to said poultry protein.

4. A fly attractant composition of claim 1 wherein:
   said poultry liver comprises dehydrated chicken livers.

5. A fly attractant composition of claim 1 wherein:
   said poultry liver comprises freeze-dried chicken liver.

6. A fly attractant composition of claim 1 wherein:
   said carbohydrate is dehydrated honey.

7. A fly attractant composition of claim 1 wherein:
   said carbohydrate fermentation microorganism is a yeast or a bacterium.

8. A fly attractant composition of claim 7 wherein:
   said yeast is chosen from the group consisting of *Saccharomyces Cerevisiae* and *Saccharomyces Carlsbergenis* and said bacterium is chosen from the group consisting of Eschericha, Clostridium, Lactobacillus, Aerobacter, Bacillus and Leuconostoc.

9. A fly attractant composition of claim 1 wherein:

said carbohydrate fermentation microorganism is a yeast.

10. A fly attractant composition of claim 9 wherein:
said yeast is Saccharomyces Cerevisiae.

11. A fly attractant composition of claim 1 wherein:
said poultry liver is present in an amount of from about 25% to about 80% by weight per the total dry weight of the ingredients;
said carbohydrate is present in an amount of from about 5% to about 40% by weight per the total dry weight of the ingredients;
said carbohydrate fermentation microorganism is present in an amount of from about 1% to about 40% by weight per the total dry weight of the ingredients.

12. A fly attractant composition of claim 11 wherein:
said carbohydrate is present in an amount of from about 15% to about 30% and said carbohydrate fermentation microorganism is present in an amount from about 10% to about 30%.

13. A fly attractant composition of claim 1 wherein:
said poultry liver comprises dehydrated chicken livers;
said carbohydrate is dehydrated honey; and
said fermentation microorganism is a yeast.

14. A fly lure consisting of:
a quantity of from about 5% to about 40% by weight per the total dry weight of the fly lure of dehydrated honey, said dehydrated honey capable of being fermented to yield carbon dioxide as a fermentation by product;
a quantity of from about 1% to about 40% by weight per the total dry weight of the fly lure of a yeast, said yeast capable of fermenting said dehydrated honey;
a quantity of from about 25% to about 80% by weight per the total dry weight of the fly lure of dehydrated chicken liver, said dehydrated chicken liver containing a digestive quantity of at least one native microorganism which is residual to chicken liver and is capable of digesting said chicken liver; and
a quantity of water sufficient to wet the other ingredients.

15. A fly lure of claim 14 wherein:
said water is present in an amount such that the total dry weight of the chicken liver, the dehydrated honey and the yeast is from about 10% to about 50% per weight of said water.

16. A method of attracting flies consisting of:
emulsifying poultry livers;
storing said emulsified poultry liver at a temperature from 50° to 75° F. for 2 to 5 days to digest said poultry liver with microorganisms native to said poultry liver;
freeze drying said microorganism containing digested poultry liver;
selecting a carbohydrate from the group consisting of dehydrated honey, fructose and dehydrated molasses which is capable of being fermented to yield carbon dioxide as a fermentation product;
selecting at least one carbohydrate fermentation microorganism, said microorganism capable of fermenting said carbohydrate to release carbon dioxide;
mixing an attractive effective amount of said digested poultry liver containing said native microorganism, a carbon dioxide producing effective amount of said carbohydrate and a fermentive quantity of said carbohydrate fermentation microorganism together;
wetting said mixture of said digested poultry liver containing said native microorganism, said carbohydrate and said carbohydrate fermentation microorganism with water to initiate further digestion of said poultry liver by said native microorganism and to initiate fermentation of said carbohydrate by said fermentation microorganism; and
exposing said wetted mixture to the atmosphere to vent vapors from said wetted mixture into the atmosphere.

17. The method of claim 16 including:
selecting chicken liver as said poultry liver.

18. The method of claim 16 including:
selecting as said carbohydrate fermentation microorganism a yeast or a bacterium chosen from the group consisting of *Saccharomyces Cerevisiae* and *Saccharomyces Carlsbergenis* yeasts and Eschericha, Clostridium, Lactobacillus, Aerobacter, Bacillus and Leuconostoc bacteria.

19. The method of claim 16 wherein:
chicken liver is selected as said poultry liver;
dehydrated honey is selected as said carbohydrate; and
*Saccharomyces Cerevisiae* is selected as said fermentation microorganism.

* * * * *